United States Patent [19]

Ikeda et al.

[11] 4,429,564
[45] Feb. 7, 1984

[54] VIBRATION TYPE DENSITY METER

[75] Inventors: Kyoichi Ikeda; Motoyoshi Ando; Kinji Harada, all of Tokyo, Japan

[73] Assignee: Yokogawa Hokushin Electric Corporation, Tokyo, Japan

[21] Appl. No.: 330,175

[22] Filed: Dec. 14, 1981

[30] Foreign Application Priority Data

Jan. 23, 1981 [JP] Japan ............................ 56-8892[U]
Jan. 23, 1981 [JP] Japan ............................ 56-8893[U]

[51] Int. Cl.$^3$ ............................................. G01N 9/00
[52] U.S. Cl. ................................................. 73/32 A
[58] Field of Search ............................. 73/32 A, 579

[56] References Cited

U.S. PATENT DOCUMENTS

| 4,217,774 | 8/1980 | Agar | 73/32 A |
| 4,297,872 | 11/1981 | Ikeda et al. | 73/32 A |
| 4,362,048 | 12/1982 | Agar et al. | 73/32 A |

OTHER PUBLICATIONS

A. P. Wenger, "Vibrating Fluid Densimeters: A Solution to the Viscosity Problem", *IEEE Transactions on Ind. Elec. and Control Instr.*, vol. IECI-27, No. 3, pp. 247-253, Aug. 1980.

*Primary Examiner*—Stephen A. Kreitman
*Attorney, Agent, or Firm*—Moonray Kojima

[57] ABSTRACT

A vibration type density meter includes a mechanical oscillator or resonator having a resonance frequency variable with the density of a specimen fluid around the oscillator. The resonator is of a cylindrical configuration with flanges at the ends thereof, at least one of the ends being open for introducing specimen fluid into the resonator. The meter also includes means for exciting the resonator, means for detecting oscillations of the cylindrical resonator, a cover coupled to the flanges of the resonator in surrounding relation to the latter, and circuit means for processing a frequency signal from the oscillation detecting means, and by arithmetic operations derive and display the density of the specimen fluid being measured.

9 Claims, 12 Drawing Figures

FIG.3
FIG.4
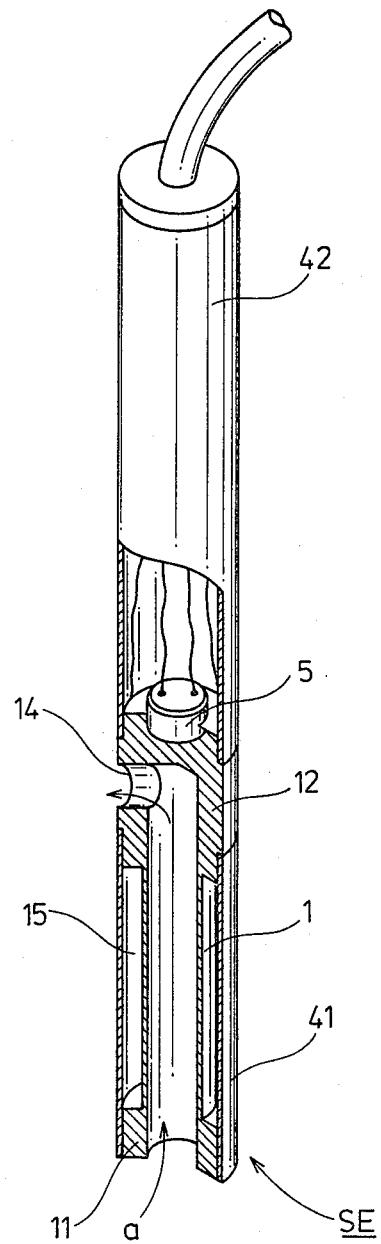
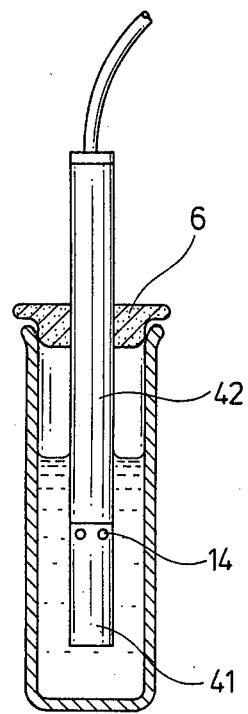

VIBRATION TYPE DENSITY METER

BACKGROUND OF THE INVENTION

1. Field of the Invention

This invention relates to a vibration type density meter including a mechanical oscillator having a resonance frequency variable with the density of a fluid around the oscillator, and more particularly to such meter usable for small amounts of fluid, and also usable on desktops, such as in a laboratory.

2. Description of the Prior Art

Various densitometers for measuring fluid densities have been proposed priorly. For example, Japanese Patent Publication No. 43-26012 discloses a density meter having a tuning fork type tubular oscillator for introducing therein a fluid to be measured for its density. The oscillator is actuated to produce transverse free oscillations, the frequency of which is utilized to derive the density of the fluid. Another density meter is disclosed in Japanese Patent Publication No. 51-16794, and comprises a cylindrical resonator, within and outside of which a fluid to be measured flows along the wall of the resonator. The density of the fluid is derived from the frequency of looped oscillation of the cylindrical resonator excited.

These prior density meters leave much to be desired. For example, the former densitometer requires a sampling pump and associated parts for introducing the fluid to be measured, into the tubular oscillator. The latter density gage is required to have its cylindrical resonator installed in a pipe through which the fluid to be measured flows. The prior density indicators, therefore, have the disadvantages of awkward installation and operation. Furthermore, the known density meters are of such a design that they are unable to measure the density of a small amount of fluid, such as a sample in a test tube.

SUMMARY OF THE INVENTION

It is an object of this invention to provide a vibration type density meter which can be handled with ease and is capable of measuring the density of a small amount of fluid.

Another object is to provide a vibration type density meter for measuring fluid densities without being adversely affected by the temperature and viscosity of fluids being measured.

According to a preferred embodiment of the present invention, a probe for use with a densitometer comprises a cylindrical resonator capable of looped oscillation having flanges at ends thereof, one of which is open to introduce a fluid to be measured therethrough into the resonator, and a cover attached to the flanges in surrounding relation to the cylindrical resonator.

The above and other objects, features, and advantages of the invention will become more apparent from the following description when taken in conjunction with the accompanying drawing in which some preferred embodiments are shown by way of illustrative examples.

BRIEF DESCRIPTION OF THE DRAWINGS

FIG. 3 depicts in perspective view, a partly cut away view of the probe of FIG. 2.

FIG. 4 depicts use of the probe to measure fluid density.

DETAILED DESCRIPTION OF PREFERRED EMBODIMENTS

Figure 1:
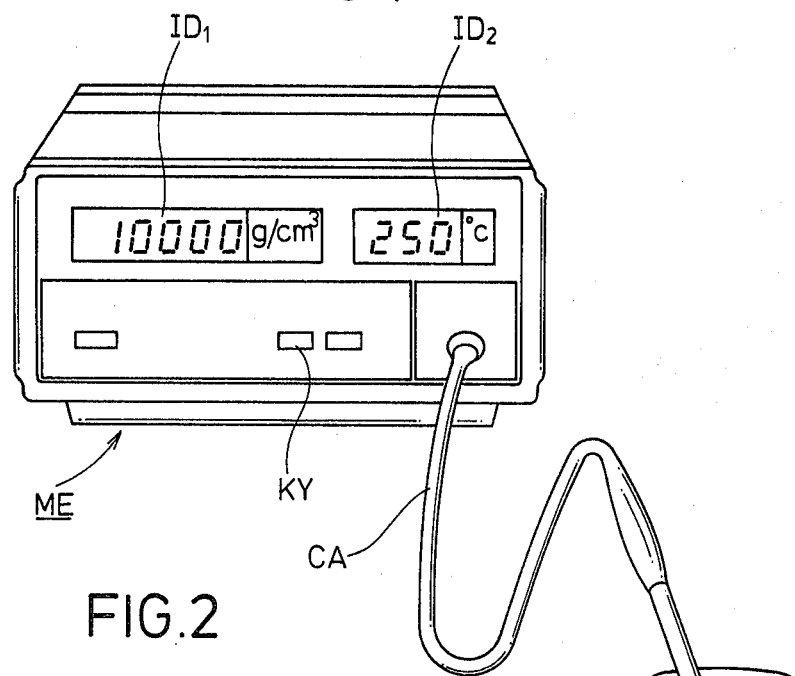
FIG. 1, depicts in pictorial view, an illustrative embodiment of the invention.

As shown in FIG. 1, a density meter according to the instant invention, includes a probe SE of an elongated rod-shaped configuration, for measuring the density of a fluid, by being inserted into the fluid, such as contained in a beaker, as shown. Probe SE is connected via a cable CA to a measuring device ME which has a display unit $ID_1$ for digital indication of a density measured, another display unit $1D_2$ for digitial indication of a temperature at which the density is being measured, and a key KY for putting the density meter in a calibration mode of operation, as explained hereinafter in greater detail.

Figure 2:
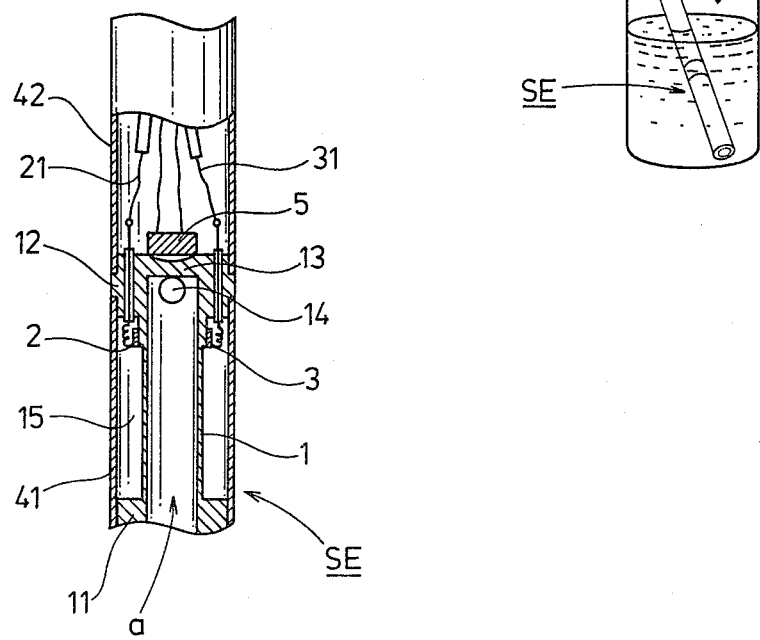
FIG. 2 depicts a cross-sectional view of an illustrative probe used in the embodiment depicted in FIG. 1.

In FIGS. 2 and 3, probe SE comprises a cylindrical resonator 1 having at one end thereof a flange 11 and at the other end thereof a flange 12 and a bottom 13 closing the other end of the resonator, as depicted. Flange 12 has a lateral through hole 14 for discharging a fluid which has entered the resonator 1 through the open end thereof (see arrow a) on which flange 11 is mounted. Flange 12 has a stepped portion to which are attached means 2 for exciting the cylindrical resonator 1 and means 3 for detecting oscillations of the cylindrical resonator 1. The means 2 and 3, are for example, composed of elements of PZT (lead zirconate titanate). Probe SE also comprises two tubular covers 41 and 42 of similar diameter. Cover 41 is connected to flanges 11 and 12, in surrounding relation to cylindrical resonator 1. Cover 42 has one end thereof coupled to flange 12 and serves as an elongated grip. Exciting means 2 and oscillation detecting means 3 are connected to cable CA by lead wires 21 and 31, respectively, which lead wires 21 and 31, respectively, extend through the cover 42. A temperature detector is mounted on bottom 13 of cylindrical resonator 1 for detecting the temperature of a fluid to be measured which is introduced in cylindrical resonator 1. Temperature detector 5 comprises a termistor or transistor, for example. Temperature detector 5 is employed for temperature compensation, and may be eliminated in many applications. define therebetween an annular chamber 15 which is filled in an air tight manner with a gas, kept at atmospheric pressure, or kept at an appropriate constant pressure, such as vacuum.

The inventive probe SE thus constructed, can be easily inserted into a specimen fluid (that is a fluid to be measured, for example for density) contained, for example, in a test tube or breaker, for measuring the density thereof. As shown in FIG. 4, a plug 6 may be used to close the open end of the test tube containing the fluid to be measured, especially when the fluid is moisture absorbent or highly volatile.

In operation, when the distal end portion of probe SE, is placed into a specimen fluid (such as shown in FIG. 1), the fluid flows into cylindrical resonator 1 in the direction of arrow a (see FIG. 2) and out through hole 14, so that the fluid fills up the interior of resonator 1. Then, a self exciting loop (not shown) including exciting means 2 and oscillation detecting means 3, is energized for looped oscillation of cylindrical resonator 1. The resonance frequency of cylindrical resonator 1 varies mainly with the density $\rho$ of the specimen fluid that fills the interior of cylindrical resonator 1. Any adverse influence due to a pressure difference between the exterior and the interior of the cylindrical resonator 1, can be removed by equalizing the pressure of the specimen fluid to the atmospheric pressure or by maintaining the fluid pressure constant. Probe SE can be relieved of temperature influences by forming cylindrical resonator 1 of a material having a small modulus of thermoelasticity, or by processing a signal delivered from temperature detector 5 for temperature compensation.

When cylindrical resonator 1 undergoes looped oscillation, with resonator 1 being filled with a specimen fluid, the resonance frequency fd of resonator 1 is related to density $\rho$ of the specimen fluid, as expressed by the following equation:

$$fd = fo(1+\alpha\rho)^{-\frac{1}{2}} \qquad (1)$$

wherein fo is the resonance frequency with density 0 (i.e. in vacuum), and $\alpha$ is a constant dependent on the diameter, thickness and others of cylindrical resonator 1.

Probe SE thus constructed is preferably rod shaped and elongated, and hence, can be handled with ease, for insertion into small amount of specimen fluid. With probe SE, no sampling pump and related parts are needed for the densitometer to effect measuring operation. Probe SE can readily be cleansed by gripping the grip part of the probe and immersing the distal end thereof in an organic solvent, for example. Furthermore, probe SE can be replaced with another similar probe without difficulty.

Figure 5:
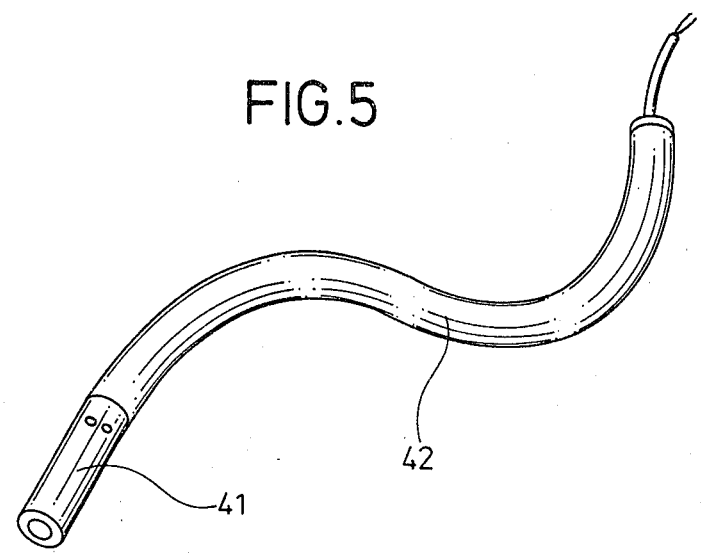
FIGS. 5 through 7 depict in perspective views, alternative embodiments of probes.

FIG. 5 shows a probe according to another embodiment. The probe includes a flexible tubular cover or grip 42 attached to a flange of a cylindrical resonator (not shown). With this arrangement, for example, the distal end of the probe can be inserted through a curved passage to reach a specimen fluid at the end of the passage. The probe of this type of construction is useful particularly when measuring the density of a fluid deep within the body of a human being or an animal.

Figures 6, 7:
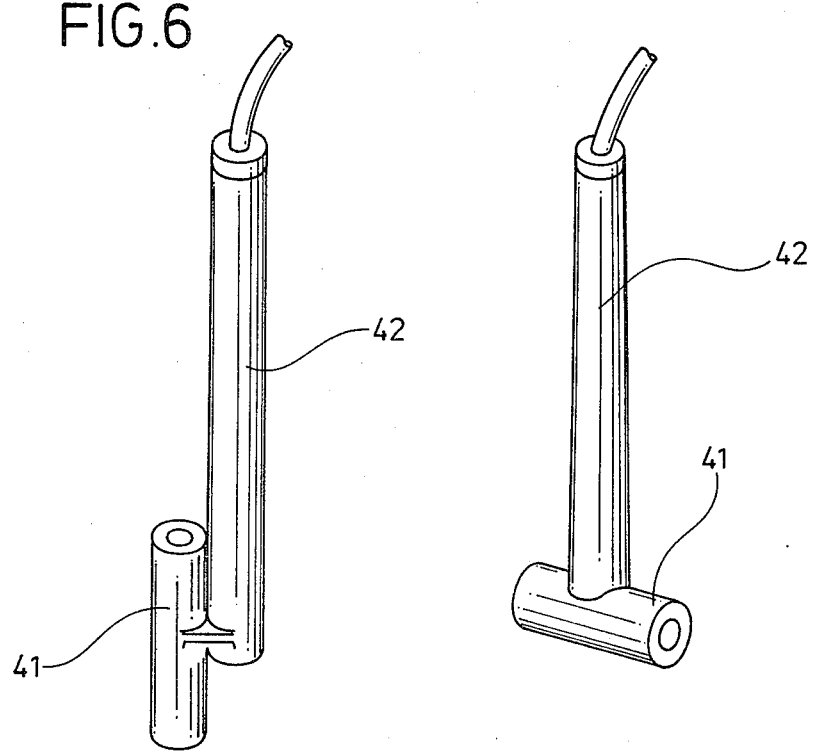

A probe shown in FIG. 6 comprises a detecting tube 41 and a grip tube 42 which are coupled together out of axial alignment with each other.

Another embodiment is depicted in FIG. 7, which shows a probe including a detecting tube 41 mounted on a distal end of a grip tube 42 so as to define a T-shaped configuration.

Each of the probes shown in FIGS. 6 and 7 comprises a cylindrical resonator (shown on the outside only) which is open at both ends thereof.

While in the foregoing embodiments, covers or tubes 41 and 42 are described or shown as being of the same or similar diameters, they may be of different diameters. Grip 42 may be joined at one end thereof to cover 41, rather than to flange 12.

Figure 8:
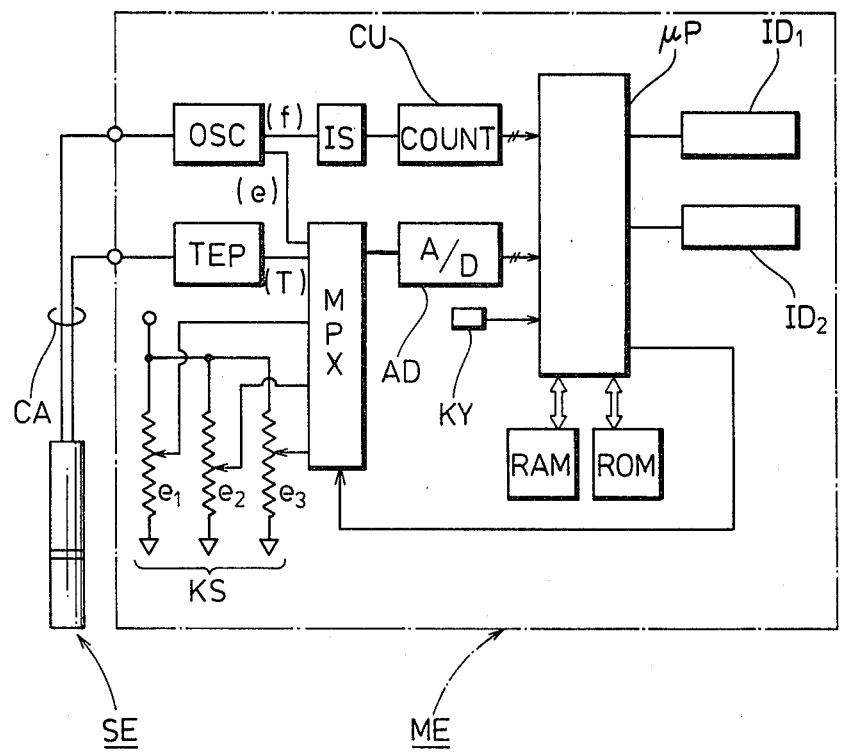
FIG. 8 depicts a block diagram of an electrical circuit used in the embodiment of FIG. 1.

FIG. 8 shows an electric circuit utilized in the measuring device ME illustrated in FIG. 1. The circuit includes an oscillator OSC supplied with a signal delivered from oscillation detecting means 3 in probe SE, for producing an output signal that is fed to exciting means 2. Thus, oscillator OSC, oscillation detecting means 3, exciting means 2, and cylindrical resonator 2 jointly define a self exciting loop for oscillating cylindrical resonator 2 at a resonance frequency. A temperature converter TEP receives a signal from temperature detecting means 5 in probe SE and produces a temperature dependent signal. A counter CU is supplied with a frequency signal f from oscillator OSC through an insolator IS and counts supplied pulses. A multiplexer MPX supplies an analog-to-digital converter AD selectively with an oscillation amplitude signal e from oscillator OSC, a temperature signal T from temperature converter TEP, and analog signals $e_1$, $e_2$, and $e_3$ produced by coefficient setting circuits or voltage dividers KS. A microprocessor $\mu P$ is supplied with a signal from counter CU and a signal from analog-to-digital converter AD and is connected to a random access memory (RAM) and a read only memory (ROM). To microprocessor $\mu P$, are also connected density indicator or unit $1D_1$ and temperature indicator or unit $1D_2$. Calibration key KY, when depressed, delivers an interrupt request signal to microprocessor $\mu P$. While in the embodiment amplitude signal e from oscillator OSC and temperature signal T from temperature converter TEP are fed though multiplexer MPX to analog-to-digital converter AD by which these signals are converted into digital signals, a voltage-to-frequency converter may instead be provided to convert amplitude signals e and temperature signal T, into frequency signals which may be converted into digital signals, by being counted by a counter. Oscillation amplitude signal e is utilized in an arithmetic operation carried out to remove any adverse affects due to the viscosity of a fluid being measured, and may be dispensed with where no consideration is given to any viscosity dependent influences.

The multiplexer MPX is suitably driven by signals from the microprocessor $\mu P$ under suitable modes of operation as discussed herein.

The circuit thus constructed, will operate as follows: At first, calibration key KY is depressed for placing the densitometer in a calibration mode of operation with probe SE exposed to ambient atmosphere. During the calibration mode, microprocessor $\mu P$ reads a digital signal related to a frequency signal fo issued from counter CU, successively reads digital signal related to an oscillation amplitude signal eo and a temperature signal To supplied from cylindrical resonator 1 as it oscillates in the air, and performs an arithmetic operation to derive a density $\rho o$ of the air at a temperature To from these read data. The data fo, eo, To, $\rho o$ are stored in the random access memory RAM.

Then, calibration key KY is released to put the densitometer in a measuring mode of operation. In this mode of operation, probe SE is placed in a specimen fluid to be measured. As in the calibration mode, microprocessor $\mu P$ reads a digital signal related to a frequency signal f from counter CU, and successively reads digital signals related to an oscillation amplitude signal e and a temperature signal T of cylindrical resonator 1 as it oscillates in the specimen fluid, and to the coefficient setting signals $e_1$, $e_2$ and $e_3$ through switching in multiplexer MPX. Then, microprocessor $\mu P$ performs arithmetic operations, as expressed by the below equations (2) and (3) on the basis of data read in the calibration and measurement modes of operation, thereby to derive the density of the specimen fluid being measured. The equations and the steps of arithmetic operations are effected in accordance with a program stored in read only memory ROM:

$$x = f/fo - 1 \tag{2}$$

$$= A[x^2 + Bx + C(x + 1)^2(eo/e - 1)] \cdot [1 + \alpha(T - To)] + \tag{3}$$

$$\rho o[1 + \beta(T - To)]$$

wherein A,B,C=constants; $\alpha$, $\beta$=temperature coefficients of the cylindrical resonator; $\rho o$=density of air; fo, eo, To=frequency oscillation amplitude, and temperature upon calibration; f,e,T=frequency, oscillation amplitude, and temperature upon measurement; and $\rho$=density of specimen fluid to be measured.

The density $\rho$ obtained through the arithmetic operations is free of influences of temperature and viscosity of the specimen fluid, and is digitally indicated on indicator $1D_1$. Temperature T is also displayed as a digital indication on indicator $1D_2$.

Theoretically speaking, only one calibration operation will suffice prior to a measuring mode of operation. However, frequency fo of natural oscillations and oscillation amplitude signal eo of the cylindrical resonator vary as the densitometer is put to frequent use or is used over a long period of time, thus resulting in a source of errors. To provide or compensate for such usages, calibration key KY should be acutated from time to time to set the densitometer in the calibration mode for updating the data such as fo, and eo. The calibration mode of operation is carried out when Key KY delivers an interrupt request signal to microprocessor $\mu P$.

The read only memory ROM stores various constants, such as temperature coefficients $\alpha,\beta$ of cylindrical resonator 1, in addition to a program for arithmetic operations in microprocessor $\mu P$. When cylindrical resonator 1 or probe SE is to be replaced, such constants must also be changed at the same time. Read only memory ROM is arranged so as to be detachable. AS many constant storing read only memories ROM are prepared, as there are probes available for use as replacements. In practice, each time a new probe replaces a previous probe, the associated read only memory ROM is installed, so that many probes are easily interchangeable together with their ROMs.

The concentration D of a specimen fluid can be known by programming the microprocessor $\mu P$ to perform an arithmetic operation expressed as follows:

$$D=(\rho-N)/M \tag{4}$$

wherein N and M are constants.

The results of the arithmetic operation are displayed as a digital indication on indicator $1D_1$ as desired. It is preferable that concentration D of the specimen fluid be converted into a value at a reference temperature for the specimen fluid. To this end, it is necessary to supply, for the arithmetic operation, data on various constants, such as the reference temperature for the specimen fluid, and primary and secondary temperature coefficients $r_1$ and $r_2$. These constants can be set by the coefficient setting circuit KS. Thus, a concentration or specific gravity, as converted into value at a reference temperature of a specimen fluid, can be obtained.

With the arrangement of the present invention, advantageously, the density meter can be calibrated in ambient atmosphere, handled with ease, and is capable of measuring the density of a small amount of specimen fluid. The probe can be easily replaced with another similar probe. The density meter is also capable of measuring the concentration or specific gravity of a specimen fluid.

Although in the illustrated embodiment, the oscillator OSC produces an oscillation amplitude signal e which is utilized in arithmetic operation to render a derived density independent of the viscosity of a specimen fluid, such a procedure may be dispensed with where the influence of viscosity need not be taken into account. The temperature indicator on the measuring device may also be dispensed with, as desired.

A process, with the viscosity $\eta$ of a specimen fluid to be measured being taken into account, will now be described. Equation (1) showing a relationship between density $\rho$ of a fluid within cylindrical resonator 1 and resonance frequency fd thereof, does not take into account, viscosity $\eta$ of a fluid to be measured.

Assuming that the viscosity of a fluid is increased, a transverse wave is generated therein and fluid components are vibrated in a direction tangential to resonator 1, as well as in a direction normal to resonator 1, with the result that the equivalent mass of the resonator is increased. Such an increase in the equivalent mass produces an indication error due to viscosity.

The mass increase L' and Q of resonator 1 due to viscosity can be derived from expressions of shearing motion as follows:

A shearing force Y in a Newtonian fluid can be given by the following equation (5):

$$Y = \eta \cdot \frac{\partial v}{\partial y} \tag{5}$$

wherein v=speed, and $\eta$=viscosity coefficient.

Due to balance of forces, the following equations result:

$$Y \cdot dA = \rho \frac{\partial v}{\partial t} \cdot (dx\,dy\,dz) \tag{6}$$

$$\therefore \rho \frac{\partial v}{\partial t} = \eta \left( \frac{\partial v^2}{\partial y^2} \right) \tag{7}$$

wherein $dA=dx \cdot dy$, and $\rho$=density.

A solution of equation (7) can be expressed by the below equation (8):

$$v = v_0 e^{-(j\omega\rho/\eta)^{\frac{1}{2}} \cdot y} \cdot e^{j\omega t} \tag{8}$$

wherein $\omega$=angular frequency.

From equations (8) and (5), an input impedance Zi of resonator 1 is given as follows:

$$Zi = -\frac{Y}{V}\bigg|y = 0 \tag{9}$$

$$= (j\omega\rho\eta)^{\frac{1}{2}} \tag{10}$$

Equation (10) can be rewritten as equation (11) hereinbelow:

$$Zi = (\tfrac{1}{2}\omega\rho\eta)^{\frac{1}{2}} + j(\tfrac{1}{2}\omega\rho\eta)^{\frac{1}{2}} \tag{11}$$

The first term of equation (11) indicates a reduction in Q due to a change in viscosity, and the second term indicates an increase in mass due to such a viscosity change. Hence, $$\frac{1}{Q} = \frac{1}{Q_t} + \frac{\omega}{k}(\tfrac{1}{2}\omega\rho\eta)^{\frac{1}{2}} \tag{12}$$

$$L' = \frac{1}{\omega}(\tfrac{1}{2}\omega\rho\eta)^{\frac{1}{2}} \tag{13}$$

wherein k=equivalent spring constant of resonantor, and $Q_o = Q$ at $\eta = 0$.

From equations (12) and (13), the following equation (14) results:

$$L' = \frac{k}{\omega^2}\left(\frac{1}{Q} - \frac{1}{Q_o}\right) \tag{14}$$

A review of equation (14) clearly shows that with k, Qo in equation (14) being constant, mass increase L' can be derived by measuring $\omega$ and Q.

A relationship between fluid density and resonance frequency is generally given by a quadratic expression. To compensate for an apparent mass increase due to viscosity; however, a density is derived using the following equation (12):

$$\rho = A \cdot \frac{1}{\omega^2} + B \cdot \frac{1}{\omega} + C - \frac{D}{\omega^2}\left(\frac{1}{Q} - \frac{1}{Q_o}\right) \tag{15}$$

wherein A, B and C and D, are constants.

In order for a self-exciting oscillation system to be oscillatable continuously, a consumed energy P and a driving energy Po should be equal to each other. These energies can be expressed as follows:

$$P = \frac{1}{Q} \cdot E_M \cdot 2\pi f \tag{16}$$

wherein $E_M$ = internally stored energy.

$$P_o = V_o^2/Z \tag{17}$$

wherein Z=input impedance, and Vo=drive voltage.

The input impedance Z is at a resonance point and hence can be given by the equation (18):

$$Z = R = \frac{1}{\omega C_o Q} \tag{18}$$

Figure 9:
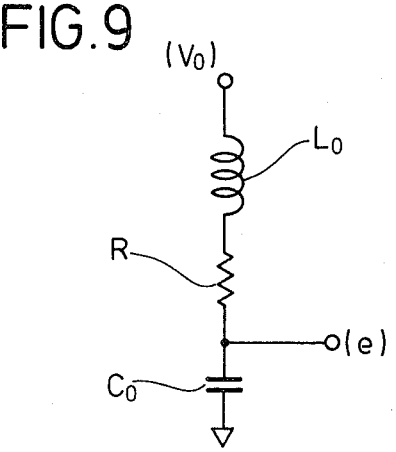
FIG. 9 is an equivalent circuit of an illustrative cylindrical resonator.

When cylindrical resonator 1 is expressed by an equivalent circuit, such as shown in FIG. 9, comprising an inductance Lo, a mechanical resistance R, and a capacitor Co, which are connected in series with each other, as depicted, the internally stored energy $E_M$ can be expressed by the equation (19):

$$E_M = \tfrac{1}{2} C_o e^2 \tag{19}$$

wherein e=oscillation amplitude.

From equations (16) through (19), a gain Av of the oscillator is given by the following equation (20):

$$A_v = \frac{V_o}{e} = \frac{1}{Q} \tag{20}$$

By substituting equation (20) in equation (15), the following equation (21) results:

$$\rho = A \cdot \frac{1}{\omega^2} + B\frac{1}{\omega} + C - \frac{D}{\omega^2}(A_v - A_{ro}) \tag{21}$$

wherein Avo=gain attained when resonator 1 is put in a vacuum.

In the circuit shown in FIG. 8, a circuit gain is measured by maintaining an output voltage Vo constant and measuring an input voltage e to obtain a signal related to Q of resonator 1. Microprocessor μP is supplied with a digital signal related to a frequency signal $\omega$ issued from counter CU and a signal related to circuit gain AV, and performs an arithmetic operation based on equation (20), for producing, as an output, a density signal $\rho$ which is free from any influence due to viscosity $\eta$.

Figure 10:
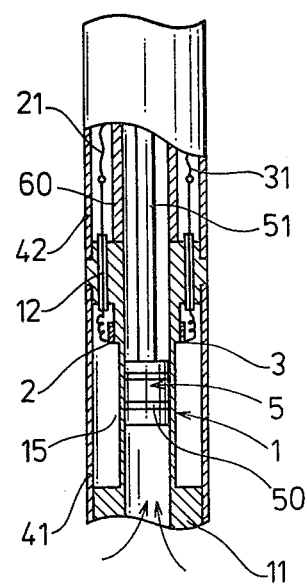
FIG. 10 is a cross sectional view of another illustrative probe.
Figure 11:
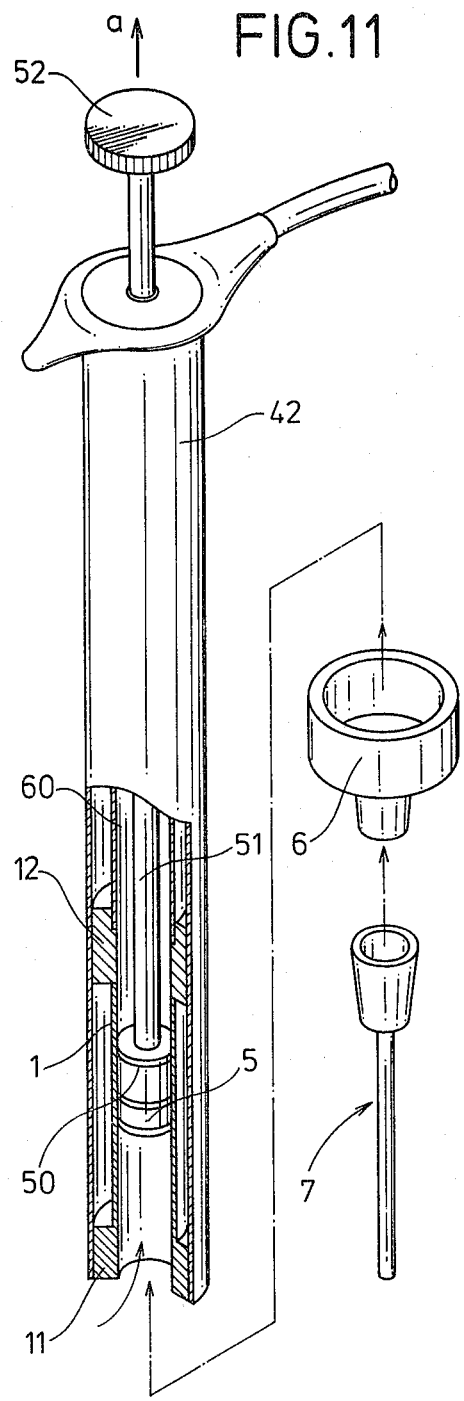
FIG. 11 depicts in perspective view, a partly cutaway view of the probe of FIG. 10.

As shown in FIGS. 10 and 11, a cylindrical resonator 1 according to another embodiment has flanges 11 and 12 at its ends, which are open. Flange 12 has a stepped portion on which are mounted means 2 for exciting cylindrical resonator 1, and means 3 for detecting oscillations of cylindrical resonator 1. Means 2 and 3 are composed of elements of PZT. A tubular cover 41 is coupled to flanges 11 and 12 in surrounding relation to cylindrical resonator 1. A tubular grip 42 has one end connected to flange 12 and covers lead wires 21 and 31 connected to exciting means 2 and oscillation detecting means 3, respectively. Tubular cover 41 and tubular grip 42 are of similar diameters. A chamber 15 which is defined between cover 41 and cylindrical resonator 1, is filled preferably with a gas kept at atmospheric pressure, or at a predetermined constant pressure (including vacuum). A piston 5 is reciprocally disposed in and held against the internal peripheral surface of cylindrical resonator 1, which serves as a cylinder. Piston 5 supports therearound, a suitable fluid tight seal 50, such as of rubber ring held against the bore surface of the cylindrical resonator 1. A rod 51 is coaxially connected at one end to piston 5 and has the other end projecting outwardly of the grip and has a knob 52 thereat. A tubular piston guide has one end attached to flange 12 and extends in coaxial relation to cylindrical resonator 1. Piston guide 60 and cylindrical resonator 1 are of the same diameter for suitable fit. Piston guide 60 extends to the end of grip 42, remote from cylindrical resonator 1, so that the probe has an uninterrupted axial hole extending from end to end.

The open distal end of resonator 1 may be equipped with a specimen collection needle 7 usable through an adapter 6.

The probe SE, thus constructed, is of an elongated rod-shaped configuration. In operation, the open distal end of the probe or collection needle 7 is put into a specimen fluid to be measured, and knob 52 is pulled in the direction of arrow a (see FIG. 11) to retract piston 5, thereby drawing specimen fluid into resonator 1 until the latter is filled with fluid.

Figure 12:
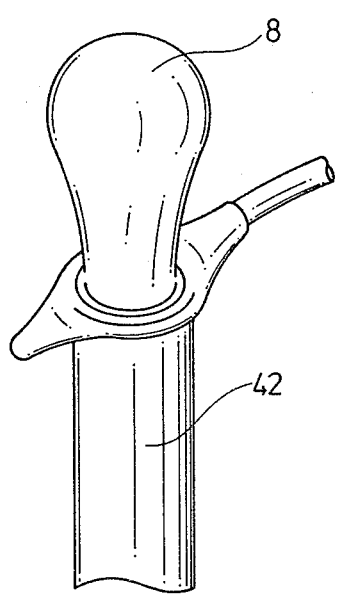
FIG. 12 depicts a fragmentary perspective view of still another probe.

According to a modification shown in FIG. 12, piston 5, rod 51, and knob 52 are replaced with a resilient ballon or bellows 8, which is affixed to the end of grip 42, remote from resonator 1.

Thus, with the arrangements shown in FIGS. 10–12, a specimen fluid can be easily drawn into resonator 1 without aid of a pump. The resonator 1 can be reliably fed with only a small amount of specimen fluid. Also, any deposits can be readily removed from the bore walls of resonator 1 by placing the distal end in a cleaning solvent and moving the piston back and forth in resonator 1, or by working the balloons or bellows 8. In the embodiment of FIG. 10,11, the piston 5 is moved upward sufficiently when drawing in the specimen fluid, so that such fluid fills the cavity of the resonator 1. Similarly, in the embodiment of FIG. 12, the flexible balloon or bellows 8, will draw sufficient specimen fluid to fill the cavity of the resonator 1. The control and measuring circuit ME, for example, will be set for a full cavity in the measuring process. Other than full cavity of resonator 1 can be used by appropriate setting of the components of circuit ME.

The foregoing description is illustrative of the principles of this invention. Numerous modifications and extensions thereof would be apparent to the worker skilled in the art. All such modifications and extensions are to be considered to be within the spirit and scope of the invention.

What is claimed is:

1. A probe for use with a vibration type density meter for measuring density of a specimen fluid, said probe comprising a cylindrical resonator means having two flanges at each end thereof, at last one of said ends being open for introducing said specimen fluid into said resonator means; a cover means rigidly fixed to said two flanges and in surrounding relation to said resonator means, said cover means and said resonator means jointly defining therebetween a chamber, said chamber being filled with a gas kept at a predetermined pressure; means for exciting said resonator means; and means for detecting a circumferential mode of oscillations of said resonator means.

2. The probe of claim 1, wherein said predetermined pressure is atmospheric pressure.

3. The probe of claim 1, wherein said means for exciting and said means for detecting each include lead wires connected to said respective means and leading out of said probe; and wherein said cover means includes an elongated grip attached to one of said flange, and covers said lead wires.

4. The probe of claim 3, wherein said elongated grip comprises a flexible tube.

5. The probe of claim 3, wherein said elongated grip is out of alignment with said cylindrical resonator means.

6. The probe of claim 3, wherein said resonator means and said elongated grip, jointly form a T-shaped configuration.

7. The probe of claim 1, wherein said resonator means includes a cylindrical tube forming said resonator, and a piston reciprocally disposed in said tube, and means for moving said piston, to thereby draw specimen fluid into said resonator tube.

8. The probe of claim 1, wherein said resonator means includes a cylindrical tube forming said resonator, and a flexible bellows attached to said tube for drawing said specimen fluid into said tube.

9. A vibration density meter for measuring density of a specimen fluid, said meter comprising at least one probe comprising a cylindrical resonator means having two flanges at each end thereof, at least one of said ends being open for introducing said specimen fluid into said resonator means; a cover means rigidly fixed to said two flanges and in surrounding relation to said resonator means, said cover means and said resonator means jointly defining therebetween a chamber, said chamber being filled with a gas kept at a predetermined pressure; means for exciting said resonator means; and means for detecting a circumferential mode of oscillations of said resonator means; means disposed within or on said resonator means for measuring the temperature thereof; wherein said detecting means further comprises a microprocessor, and means for supplying to said microprocessor a signal related to a resonant frequency of said resonator means and a signal related to said temperature of said resonator means, whereby during a calibration mode of operation, said resonator means is exposed to air and said microprocessor is supplied with a signal related to a resonance frequency fo of said resonator means, and a signal related to a temperature To thereof, thereby causing said microprocessor to derive a density $\rho o$ of air through arithmetic operation; and whereby during a measuring mode of operation, said resonator means is placed in said specimen fluid and said microprocessor is supplied with a signal related to resonance frequency f of said resonator means and a signal related to temperature T thereof, thereby causing said microprocessor to derive a density of said specimen fluid through an arithmetic operation, using data obtained during said calibration mode and said measuring mode, and means for displaying the results of said arithmethic operations; and wherein further is provided at least one read only memory unit associated with said at least one probe, for storing constants of said at least one probe, with said at least one probe being used together with said associated at least one read only memory unit; and wherein said microprocessor is arranged to effect an arithmetic operation in response to a signal related to a circuit gain of an oscillator, including said resonator means; thereby deriving a density signal free from any influence of viscosity of said specimen fluid.

* * * * *